(12) United States Patent
Lemont (10) Patent No.: US 12,408,608 B2
(45) Date of Patent: Sep. 9, 2025

(54) LETTUCE VARIETY 'EZPARK'

(71) Applicant: Enza Zaden Beheer B.V., Enkhuizen (NL)

(72) Inventor: Magali Lemont, Longue (FR)

(73) Assignee: Enza Zaden Beheer B.V., Enkhuizen (NL)

( * ) Notice: Subject to any disclaimer, the term of this patent is extended or adjusted under 35 U.S.C. 154(b) by 229 days.

(21) Appl. No.: 18/125,282

(22) Filed: Mar. 23, 2023

(65) Prior Publication Data

US 2023/0301260 A1    Sep. 28, 2023

Related U.S. Application Data

(60) Provisional application No. 63/323,022, filed on Mar. 23, 2022.

(51) Int. Cl.
*A01H 6/14* (2018.01)
*A01H 5/12* (2018.01)

(52) U.S. Cl.
CPC ............ *A01H 6/1472* (2018.05); *A01H 5/12* (2013.01)

(58) Field of Classification Search
None
See application file for complete search history.

(56) References Cited

U.S. PATENT DOCUMENTS 7,371,934 B1 *  5/2008  Skrsyniarz ............... A01H 5/12
                                                        800/278

* cited by examiner

*Primary Examiner* — Shubo (Joe) Zhou
*Assistant Examiner* — David R Byrnes
(74) *Attorney, Agent, or Firm* — Foley Hoag LLP; Brendan T. Jones; David E. Shore (57) ABSTRACT

A new lettuce variety designated 'Ezpark' is described. 'Ezpark' is a lettuce variety exhibiting stability and uniformity.

18 Claims, 8 Drawing Sheets
(8 of 8 Drawing Sheet(s) Filed in Color)

LETTUCE VARIETY 'EZPARK'

CROSS-REFERENCE TO RELATED APPLICATIONS

This application claims the benefit of priority to U.S. Provisional Application No. 63/323,022, filed on Mar. 23, 2022; the entire content of which is hereby incorporated by reference.

FIELD

The present disclosure relates to the field of plants and plant breeding. In particular, this disclosure includes new lettuce, Lactuca sativa, variety designated 'Ezpark'.

BACKGROUND

Cultivated forms of lettuce belong to the highly polymorphic species Lactuca sativa that is grown for its edible head and leaves. As a crop, lettuce is grown commercially wherever environmental conditions permit the production of an economically viable yield. For planting purposes, the lettuce season is typically divided into three categories (i.e., early, mid, and late), with coastal areas planting from January to August, and desert regions planting from August to December. Fresh lettuce is consumed nearly exclusively as fresh, raw product and occasionally as a cooked vegetable.

Lactuca sativa is in the Cichorieae tribe of the Asteraceae (Compositae) family. Lettuce is related to chicory, sunflower, aster, dandelion, artichoke, and *chrysanthemum*. *Sativa* is one of about 300 species in the genus *Lactuca*. There are seven different morphological types of lettuce. The crisphead group includes the iceberg and batavian types. Iceberg lettuce has a large, firm head with a crisp texture and a white or creamy yellow interior. The batavian lettuce predates the iceberg type and has a smaller and less firm head. The butterhead group has a small, soft head with an almost oily texture. The romaine, also known as cos lettuce, has elongated upright leaves forming a loose, loaf-shaped head and the outer leaves are usually dark green. Leaf lettuce, also known as cutting lettuce, comes in many varieties, none of which form a head, and include the green oak leaf variety. Latin lettuce, also known as grasse-type lettuce, looks like a cross between romaine and butterhead. Stem lettuce has long, narrow leaves and thick, edible stems. Oilseed lettuce is a type grown for its large seeds that are pressed to obtain oil.

SUMMARY

Lettuce is an increasingly popular crop. Worldwide lettuce consumption continues to increase. As a result of this demand, there is a continued need for new lettuce varieties. In particular, there is a need for improved lettuce varieties that are stable, high yielding, and agronomically sound. In order to meet these needs, the present disclosure is directed to improved lettuce varieties.

In one embodiment, the present disclosure is directed to lettuce, Lactuca sativa, seed designated as 'Ezpark' having NCIMB Accession Number 44138. In one embodiment, the present disclosure is directed to a Lactuca sativa lettuce plant and parts isolated therefrom produced by growing 'Ezpark' lettuce seed (which plants and parts can be referred to, e.g., as 'Ezpark' plants and 'Ezpark' parts, respectively). In another embodiment, the present disclosure is directed to a Lactuca sativa plant and/or parts isolated therefrom, having all or essentially all the physiological and morphological characteristics of a Lactuca sativa plant produced by growing 'Ezpark' lettuce seed having NCIMB Accession Number 44138. In still another embodiment, the present disclosure is directed to an $F_1$ hybrid Lactuca sativa lettuce seed, plants grown from the seed, and/or a leaf isolated therefrom having 'Ezpark' as a parent, where 'Ezpark' is grown from 'Ezpark' lettuce seed having NCIMB Accession Number 44138.

Lettuce plant parts include lettuce hearts, lettuce leaves, parts of lettuce leaves, pollen, ovules, flowers, and the like. In another embodiment, the present disclosure is further directed to lettuce leaves, parts of lettuce leaves, flowers, pollen, and/or ovules isolated from 'Ezpark' lettuce plants. In another embodiment, the present disclosure is further directed to tissue culture of 'Ezpark' lettuce plants, and/or to lettuce plants regenerated from the tissue culture, where the plants regenerated from the issue culture have all, or essentially all, of the morphological and physiological characteristics of 'Ezpark' lettuce plants.

In still another embodiment, the present disclosure is further directed to packaging material containing 'Ezpark' plant parts. Such packaging material includes but is not limited to boxes, plastic bags, etc. The 'Ezpark' plant parts may be combined with other plant parts of other plant varieties.

In yet another embodiment, the present disclosure is further directed to a method of selecting lettuce plants, by (a) growing 'Ezpark' lettuce plants where the 'Ezpark' plants are grown from lettuce seed having NCIMB Accession Number 44138 and (b) selecting a plant from step (a). In another embodiment, the present disclosure is further directed to lettuce plants, plant parts and/or seeds produced by the lettuce plants where the lettuce plants are isolated by the selection method of the disclosure.

In another embodiment, the present disclosure is further directed to a method of breeding lettuce plants by crossing a lettuce plant with a plant grown from 'Ezpark' lettuce seed having NCIMB Accession Number 44138. In still another embodiment, the present disclosure is further directed to lettuce plants, lettuce parts from the lettuce plants, and/or seeds produced therefrom where the lettuce plant is isolated by the breeding method of the disclosure.

In another embodiment, the present disclosure is directed to methods of producing 'Ezpark'-derived lettuce seeds by crossing an 'Ezpark' lettuce plant with itself or a second lettuce plant, and harvesting seeds of an 'Ezpark'-derived lettuce plant. In another embodiment, the method for producing seeds of 'Ezpark'-derived lettuce seeds further includes crossing a plant grown from an 'Ezpark'-derived lettuce seed with itself or a second lettuce plant to yield additional 'Ezpark'-derived lettuce seeds, growing the additional 'Ezpark'-derived lettuce seeds to yield additional 'Ezpark'-derived lettuce plants, and repeating the crossing and growing steps for 3-10 generations to generate additional 'Ezpark'-derived lettuce plants.

In another embodiment, the present disclosure is directed to methods for producing a male sterile lettuce plant by introducing a nucleic acid molecule that confers male sterility into a lettuce plant produced by growing 'Ezpark' lettuce seed, and/or to male sterile lettuce plants produced by such methods.

In another embodiment, the present disclosure is directed to methods of producing an herbicide resistant lettuce plant by introducing a gene conferring herbicide resistance into a lettuce plant produced by growing 'Ezpark' lettuce seed, where the gene confers resistance to an herbicide selected from glyphosate, sulfonylurea, imidazolinone, dicamba, glufosinate, phenoxy proprionic acid, L-phosphinothricin, cyclohexone, cyclohexanedione, triazine, and benzonitrile. Certain embodiments are also directed to herbicide resistant lettuce plants produced by such methods.

In another embodiment, the present disclosure is directed to methods of producing a pest or insect resistant lettuce plan by introducing a gene conferring pest or insect resistance into a lettuce plant produced by growing 'Ezpark' lettuce seed, and/or to pest or insect resistant lettuce plants produced by such methods. In certain embodiments, the gene conferring pest or insect resistance encodes a *Bacillus thuringiensis* endotoxin.

In another embodiment, the present disclosure is directed to methods of producing a disease resistant lettuce plant by introducing a gene conferring disease resistance into a lettuce plant produced by growing 'Ezpark' lettuce seed, and/or to disease resistant lettuce plants produced by such methods.

In another embodiment, the present disclosure is directed to methods of producing a lettuce plant with a value-added trait by introducing a gene conferring a value-added trait into a lettuce plant produced by growing 'Ezpark' lettuce seed, where the gene encodes a protein selected from a ferritin, a nitrate reductase, and a monellin. Certain embodiments are also directed to lettuce plants having a value-added trait produced by such methods.

In another embodiment, the present disclosure is directed to methods of introducing a desired trait into lettuce variety 'Ezpark', by: (a) crossing a 'Ezpark' plant, where a sample of 'Ezpark' lettuce seed was deposited under NCIMB Accession Number 44138, with a plant of another lettuce variety that contains a desired trait to produce progeny plants, where the desired trait is selected from male sterility; herbicide resistance; insect or pest resistance; modified bolting; and resistance to bacterial disease, fungal disease or viral disease; (b) selecting one or more progeny plants that have the desired trait; (c) backcrossing the selected progeny plants with a 'Ezpark' plant to produce backcross progeny plants; (d) selecting for backcross progeny plants that have the desired trait and all, or essentially all, of the physiological and morphological characteristics of lettuce variety 'Ezpark'; and (e) repeating steps (c) and (d) two or more times in succession to produce selected third or higher backcross progeny plants that comprise the desired trait. Certain embodiments are also directed to lettuce plants produced by such methods, where the plants have the desired trait and all, or essentially all, of the physiological and morphological characteristics of lettuce variety 'Ezpark'. In certain embodiments, the desired trait is herbicide resistance and/or the resistance is conferred to an herbicide selected from glyphosate, sulfonylurea, imidazolinone, dicamba, glufosinate, phenoxy proprionic acid, L-phosphinothricin, cyclohexone, cyclohexanedione, triazine, and benzonitrile.

In another embodiment, the present disclosure provides for single gene converted plants of 'Ezpark'. The single transferred gene may preferably be a dominant or recessive allele. Preferably, the single transferred gene will confer such traits as male sterility, herbicide resistance, insect or pest resistance, modified fatty acid metabolism, modified carbohydrate metabolism, resistance for bacterial, fungal, or viral disease, male fertility, enhanced nutritional quality, and/or industrial usage.

In a further embodiment, the present disclosure relates to methods for developing lettuce plants in a lettuce plant breeding program using plant breeding techniques including recurrent selection, backcrossing, pedigree breeding, restriction fragment length polymorphism enhanced selection, and/or genetic marker enhanced selection. Seeds, lettuce plants, and parts thereof, produced by such breeding methods are also part of the disclosure.

In addition to the exemplary aspects and embodiments described above, further aspects and embodiments will become apparent by reference by study of the following description.

BRIEF DESCRIPTION OF THE DRAWINGS

The patent or application file contains at least one drawing executed in color. Copies of this patent or patent application publication with color drawings will be provided by the office upon request and payment of the necessary fee.

FIGS. 1A-1D show photos of lettuce variety 'Ezpark'.

FIGS. 2A-2D show side-by-side comparisons of lettuce variety 'Ezpark' with commercial lettuce varieties 'Eztron' and 'Ezrilla'.

DETAILED DESCRIPTION

There are numerous steps in the development of novel, desirable lettuce germplasm. Plant breeding begins with the analysis of problems and weaknesses of current lettuce germplasms, the establishment of program goals, and the definition of specific breeding objectives. The next step is selection of germplasm that possess the traits to meet the program goals. The goal is to combine in a single variety or hybrid an improved combination of desirable traits from the parental germplasm. These important traits may include, among other things, increased head size and weight, higher seed yield, improved color, resistance to diseases and insects, tolerance to drought and heat, and better agronomic quality.

Choice of breeding or selection methods can depend on the mode of plant reproduction, the heritability of the trait(s) being improved, and the type of variety used commercially (e.g., $F_1$ hybrid variety, pureline variety). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable variety. This approach has been used extensively for breeding disease-resistant varieties. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program may include a periodic, objective evaluation of the efficiency of the breeding procedure. Evaluation criteria vary depending on the goal and objectives, and can include gain from selection per year based on comparisons to an appropriate standard, the overall value of the advanced breeding lines, and the number of successful varieties produced per unit of input (e.g., per year, per dollar expended).

Promising advanced breeding lines may be thoroughly tested and compared to appropriate standards in environments representative of the commercial target area(s) for at least three years. The best lines can then be candidates for new commercial varieties. Those still deficient in a few traits may be used as parents to produce new populations for further selection. These processes, which lead to the final step of marketing and distribution, may take from ten to twenty years from the time the first cross or selection is made.

One goal of lettuce plant breeding is to develop new, unique, and genetically superior lettuce varieties. A breeder can initially select and cross two or more parental lines, followed by repeated selfing and selection, producing many new genetic combinations. Moreover, a breeder can generate multiple different genetic combinations by crossing, selfing, and mutations. A plant breeder can then select which germplasms to advance to the next generation. These germplasms may then be grown under different geographical, climatic, and soil conditions, and further selections can be made during, and at the end of, the growing season.

The development of commercial lettuce varieties thus requires the development and/or selection of parental lettuce varieties, the crossing of these varieties, and the evaluation of the crosses. Pedigree breeding and recurrent selection breeding methods may be used to develop varieties from breeding populations. Breeding programs can be used to combine desirable traits from two or more varieties or various broad-based sources into breeding pools from which new varieties are developed by selfing and selection of desired phenotypes. The new varieties are crossed with other varieties and the hybrids from these crosses are evaluated to determine which have commercial potential.

Pedigree breeding is generally used for the improvement of self-pollinating crops or inbred lines of cross-pollinating crops. Two parents which possess favorable, complementary traits are crossed to produce an $F_1$. An $F_2$ population is produced by selfing one or several $F_1$s or by intercrossing two $F_1$s (sib mating). Selection of the best individuals is usually begun in the $F_2$ population. Then, beginning in the $F_3$, the best individuals in the best families are selected. Replicated testing of families, or hybrid combinations involving individuals of these families, often follows in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new varieties.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding may be used to transfer one or more genes for a simply inherited, highly heritable trait into a desirable homozygous cultivar or line that is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

New varieties can also be developed from more than two parents. The technique, known as modified backcrossing, uses different recurrent parents during the backcrossing. Modified backcrossing may be used to replace the original recurrent parent with a variety having certain more desirable characteristics or multiple parents may be used to obtain different desirable characteristics from each.

In addition to being used to create a backcross conversion, backcrossing can also be used in combination with pedigree breeding. As discussed previously, backcrossing can be used to transfer one or more specifically desirable traits from one variety, the donor parent, to a developed variety called the recurrent parent, which has overall good agronomic characteristics yet lacks that desirable trait or traits. However, the same procedure can be used to move the progeny toward the genotype of the recurrent parent, but at the same time retain many components of the nonrecurrent parent by stopping the backcrossing at an early stage and proceeding with selfing and selection. For example, an inbred lettuce line may be crossed with another variety to produce a first generation progeny plant. The first generation progeny plant may then be backcrossed to one of its parent varieties to create a BC1 or BC2. Progeny are selfed and selected so that the newly developed variety has many of the attributes of the recurrent parent and yet several of the desired attributes of the nonrecurrent parent. This approach leverages the value and strengths of the recurrent parent for use in new lettuce varieties.

In some embodiments, the single-seed descent procedure may refer to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines with each generation due to failure of some seeds to germinate or some plants to produce at least one seed. As a result, not all of the $F_2$ plants originally sampled in the population will be represented by a progeny when generation advance is completed.

In addition to phenotypic observations, the genotype of a plant can also be examined. There are many laboratory-based techniques known in the art that are available for the analysis, comparison and characterization of plant genotype. Such techniques include, without limitation, High Resolution Melting (HRM), DNA- or RNA-sequencing, CAPS Markers, ELISA, Western blot, microarrays, Single Nucleotide Polymorphisms (SNPs), Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), Differential Display Polymerase Chain Reaction (DD-PCR), Quantitative Real-Time Polymerase Chain Reaction (qRT-PCR), DNA Amplification Fingerprinting (DAF), Sequence Characterized Amplified Regions (SCARs), Amplified Fragment Length Polymorphisms (AFLPs), and Simple Sequence Repeats (SSRs, which are also referred to as Microsatellites).

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select toward the genome of the recurrent parent and against the markers of the donor parent. This procedure attempts to minimize the amount of genome from the donor parent that remains in the selected plants. It can also be used to reduce the number of crosses back to the recurrent parent needed in a backcrossing program. The use of molecular markers in the selection process is often called genetic marker enhanced selection or marker-assisted selection. Molecular markers may also be used to identify and exclude certain sources of germplasm as parental varieties or ancestors of a plant by providing a means of tracking genetic profiles through crosses.

Mutation breeding may also be used to introduce new traits into lettuce varieties. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation (such as X-rays, Gamma rays, neutrons, Beta radiation, or ultraviolet radiation), chemical mutagens (such as base analogs like 5-bromo-uracil), antibiotics, alkylating agents (such as sulfur mustards, nitrogen mustards, epoxides, ethyleneamines, sulfates, sulfonates, sulfones, or lactones), azide, hydroxylamine, nitrous acid, or acridines. Once a desired trait is observed through mutagenesis the trait may then be incorporated into existing germplasm by traditional breeding techniques. Details of mutation breeding can be found in *Principles of Cultivar Development* by Fehr, Macmillan Publishing Company (1993).

The production of double haploids can also be used for the development of homozygous varieties in a breeding program. Double haploids are produced by the doubling of a set of chromosomes from a heterozygous plant to produce a completely homozygous individual. For example, see Wan, et al., *Theor. Appl. Genet.*, 77:889-892 (1989).

Additional non-limiting examples of breeding methods that may be used include, without limitation, those found in *Principles of Plant Breeding*, John Wiley and Son, pp. 115-161 (1960); Allard (1960); Simmonds (1979); Sneep, et al. (1979); Fehr (1987); and "Carrots and Related Vegetable *Umbelliferae*," Rubatzky, V. E., et al. (1999).

Definitions

In the description that follows, a number of terms are used. In order to provide a clear and consistent understanding of the specification and claims, including the scope to be given such terms, the following definitions are provided:

Allele. The allele is any of one or more alternative forms of a gene, all of which relate to one trait or characteristic. In a diploid cell or organism, the two alleles of a given gene occupy corresponding loci on a pair of homologous chromosomes.

Backcrossing. Backcrossing is a process in which a breeder repeatedly crosses hybrid progeny back to one of the parents, for example, a first generation hybrid $F_1$ with one of the parental genotypes of the $F_1$ hybrid.

Bolting. The premature development of a flowering stalk, and subsequent seed, before a plant produces a food crop. Bolting is typically caused by late planting.

*Bremia lactucae*. An oomycete that causes downy mildew in lettuce in cooler growing regions.

Core length. Length of the internal lettuce stem measured from the base of the cut and trimmed plant to the tip of the stem.

Corky root. A disease caused by the bacterium *Rhizomonas suberifaciens*, which causes the entire taproot to become brown, severely cracked, and non-functional.

Cotyledon. One of the first leaves of the embryo of a seed plant; typically one or more in monocotyledons, two in dicotyledons, and two or more in gymnosperms.

Essentially all the physiological and morphological characteristics. A plant having essentially all the physiological and morphological characteristics means that the plants share essentially all physiological and morphological characteristics identified herein, except, e.g., with respect to characteristics derived from a converted gene that differs between the plants as a result backcrossing, mutation, or genetic engineering.

First water date. The date the seed first receives adequate moisture to germinate. This can and often does equal the planting date.

Gene. As used herein, "gene" refers to a segment of nucleic acid. A gene can be introduced into a genome of a species, whether from a different species or from the same species, using transformation or various breeding methods.

Plant diameter. Diameter of the cut and trimmed plant, sliced vertically, and measured at the widest point perpendicular to the stem.

Plant height. Height of the cut and trimmed plant, sliced vertically, and measured from the base of the cut stem to the cap leaf.

Plant weight. Weight of saleable lettuce head, cut and trimmed to market specifications.

Lettuce die-back. A disease that can cause a stunted plant with yellowed outer leaves that can develop necrotic spots and lesions, and dark green inner leaves that can be rough and leathery. Lettuce dieback is a soil-borne disease caused by two closely related viruses from the family Tombusviridae—Tomato Bushy Stunt Virus (TBSV) and Lettuce Necrotic Stunt Virus (LNSV).

Lettuce Mosaic virus. A disease that can cause a stunted, deformed, or mottled pattern in young lettuce and yellow, twisted, and deformed leaves in older lettuce.

Maturity date. Maturity refers to the stage when the plants are of full size or optimum weight, in marketable form or shape to be of commercial or economic value.

*Nasonovia ribisnigri*. A lettuce aphid that colonizes the innermost leaves of the lettuce plant, contaminating areas that cannot be treated easily with insecticides.

Quantitative Trait Loci. Quantitative Trait Loci (QTL) refers to genetic loci that control to some degree, numerically representable traits that are usually continuously distributed.

Ratio of plant height/diameter. Plant height divided by the head diameter is an indication of the plant shape; <1 is flattened, 1=round, and >1 is pointed.

Regeneration. Regeneration refers to the development of a plant from tissue culture.

RHS. RHS refers to the Royal Horticultural Society of England which publishes an official botanical color chart quantitatively identifying colors according to a defined numbering system. The chart may be purchased from Royal Horticulture Society Enterprise Ltd., RHS Garden; Wisley, Woking; Surrey GU236QB, UK.

Single gene converted. Single gene converted or conversion plant refers to plants which are developed by a plant breeding technique called backcrossing or via genetic engineering where essentially all of the desired morphological and physiological characteristics of a line are recovered in addition to the single gene transferred into the line via the backcrossing technique or via genetic engineering.

Tip burn. Means a browning of the edges or tips of lettuce leaves that is a physiological response to a lack of calcium.

Wet date. The wet date corresponds to the first planting date of lettuce.

Overview of the Variety 'Ezpark'

Figure 1A:
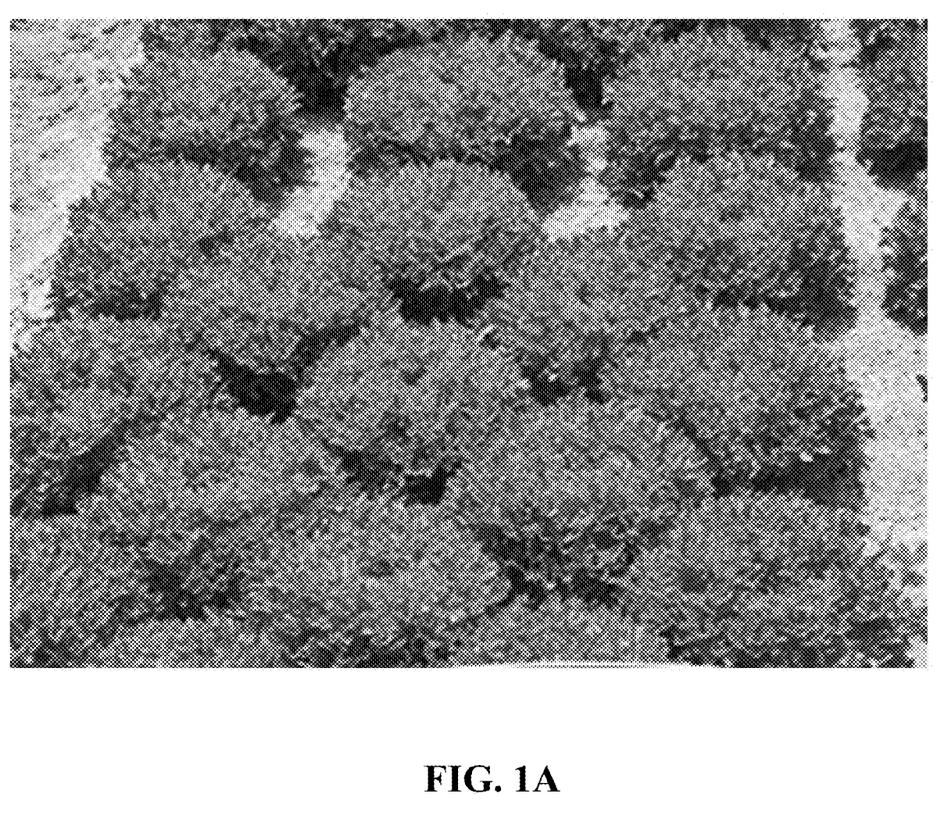
FIG. 1A shows whole plants and harvest-mature outer leaves of lettuce variety 'Ezpark'.
Figure 1B:
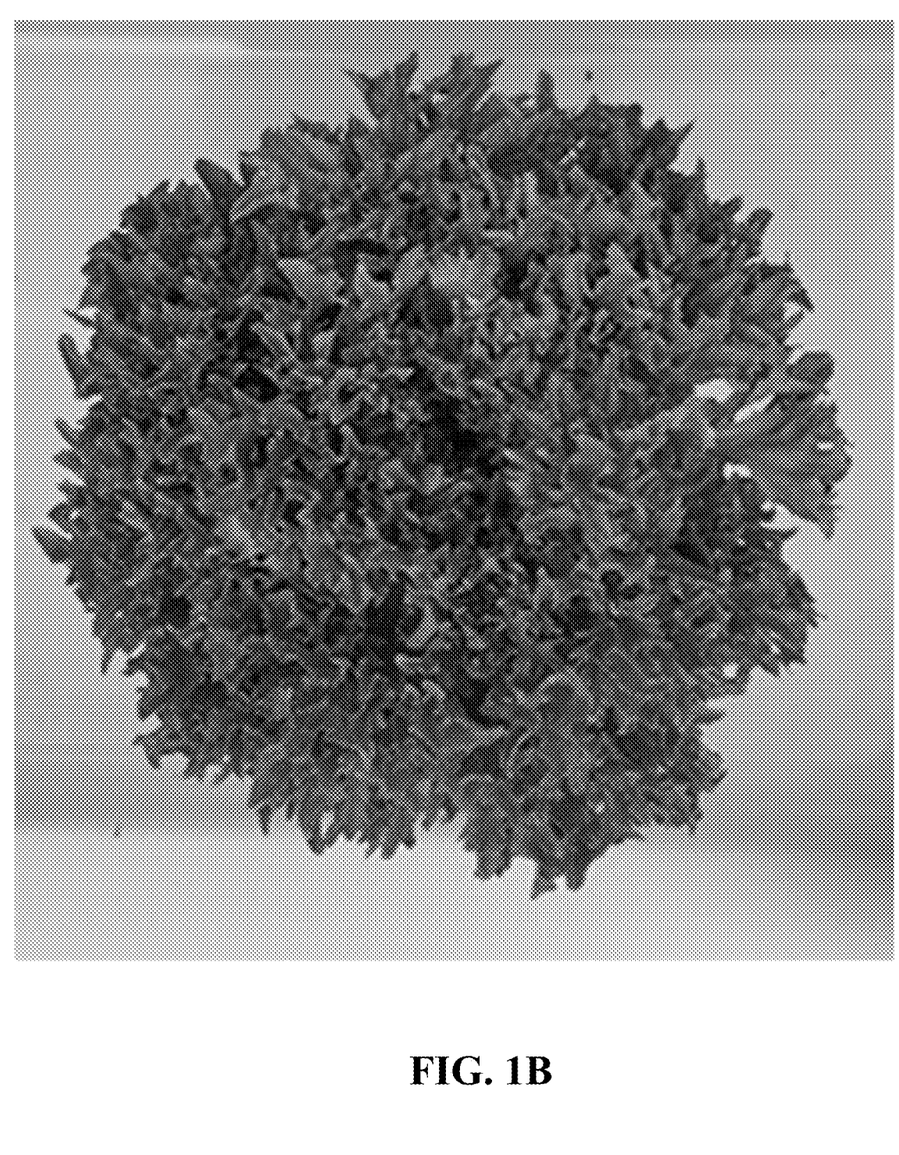
FIG. 1B shows a top view of a whole plant of lettuce variety 'Ezpark'.
Figure 1C:
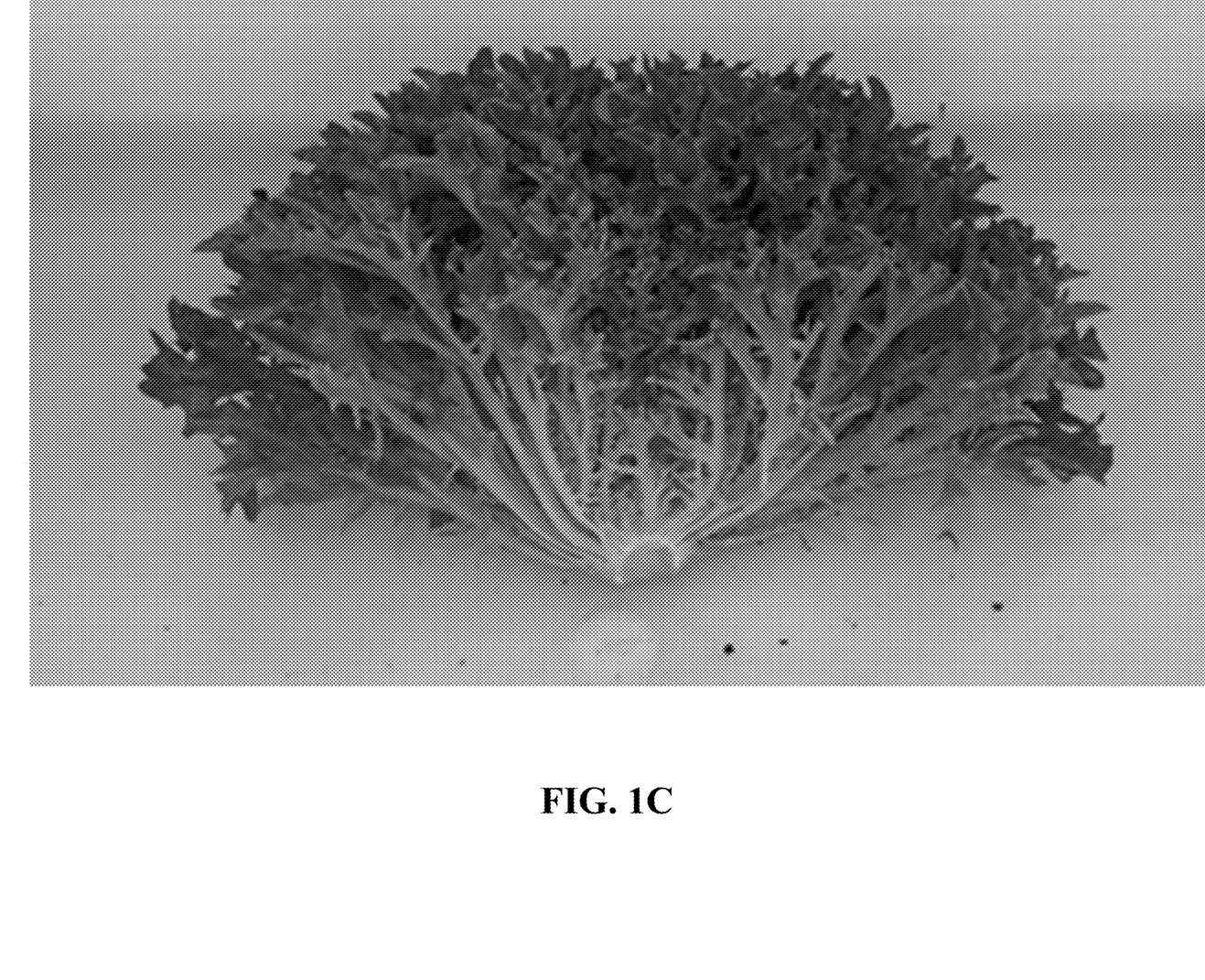
FIG. 1C shows a longitudinal section of a harvest mature plant of lettuce variety 'Ezpark'.
Figure 1D:
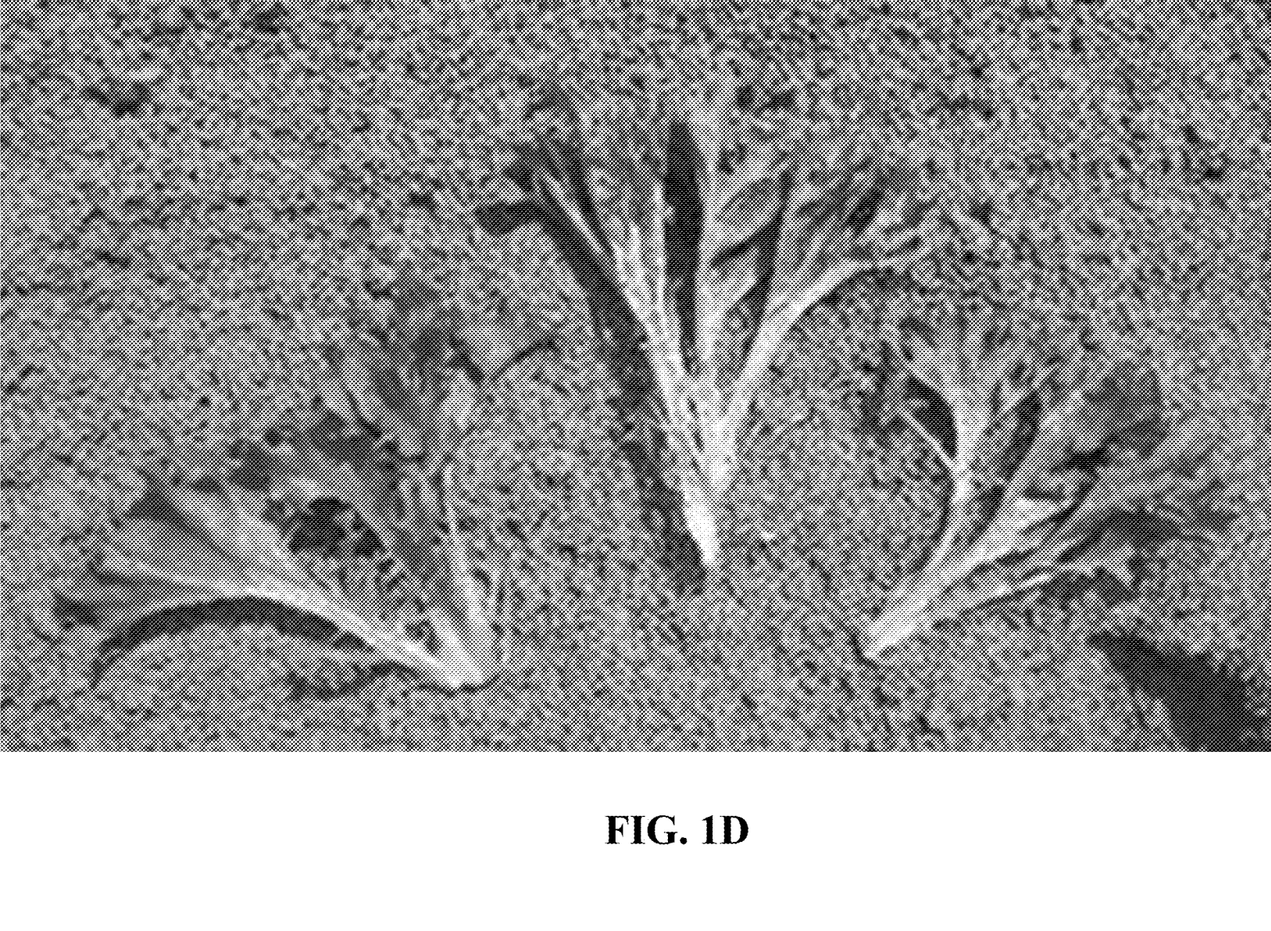
FIG. 1D shows harvest-mature outer leaves of lettuce variety 'Ezpark'.
Figure 2A:
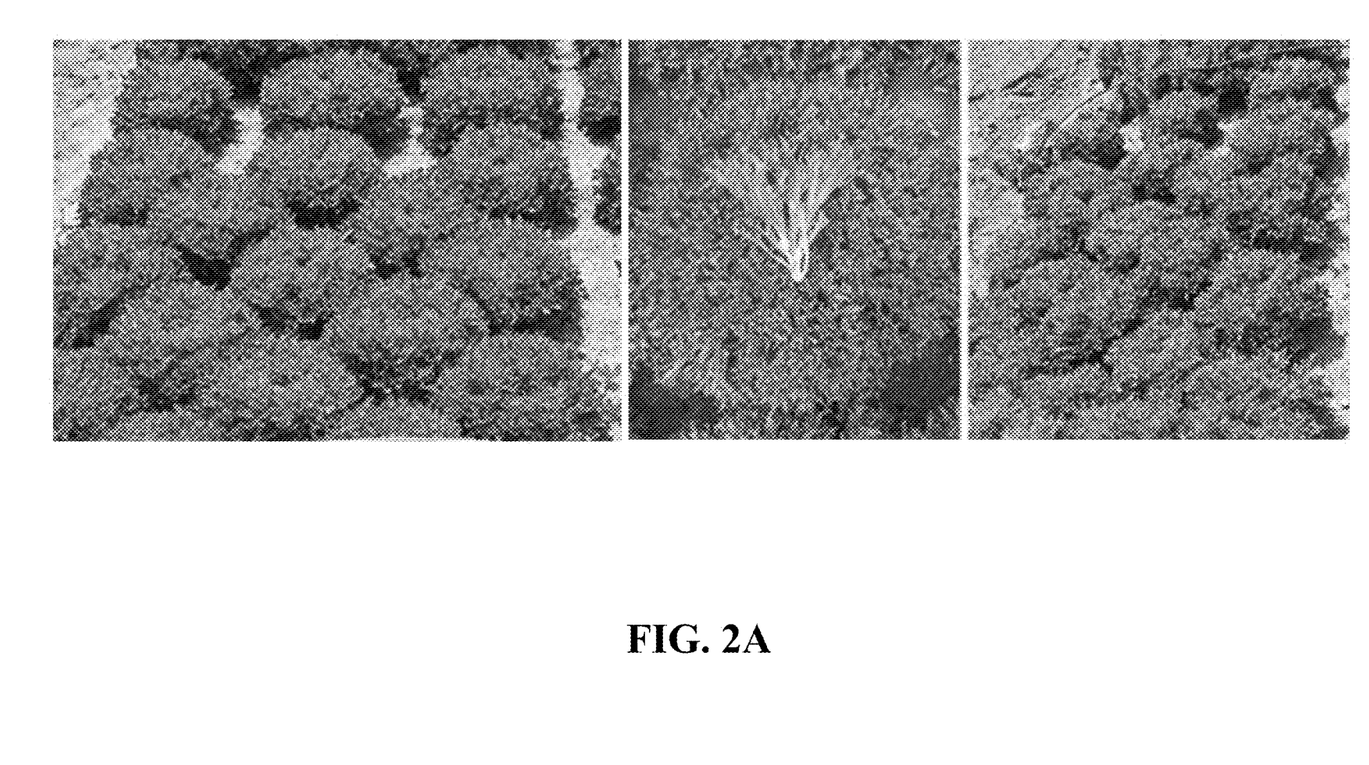
FIG. 2A shows a side-by-side comparison of whole plants of lettuce varieties 'Ezpark' (left), 'Eztron (middle), and 'Ezrilla' (right).
Figure 2B:
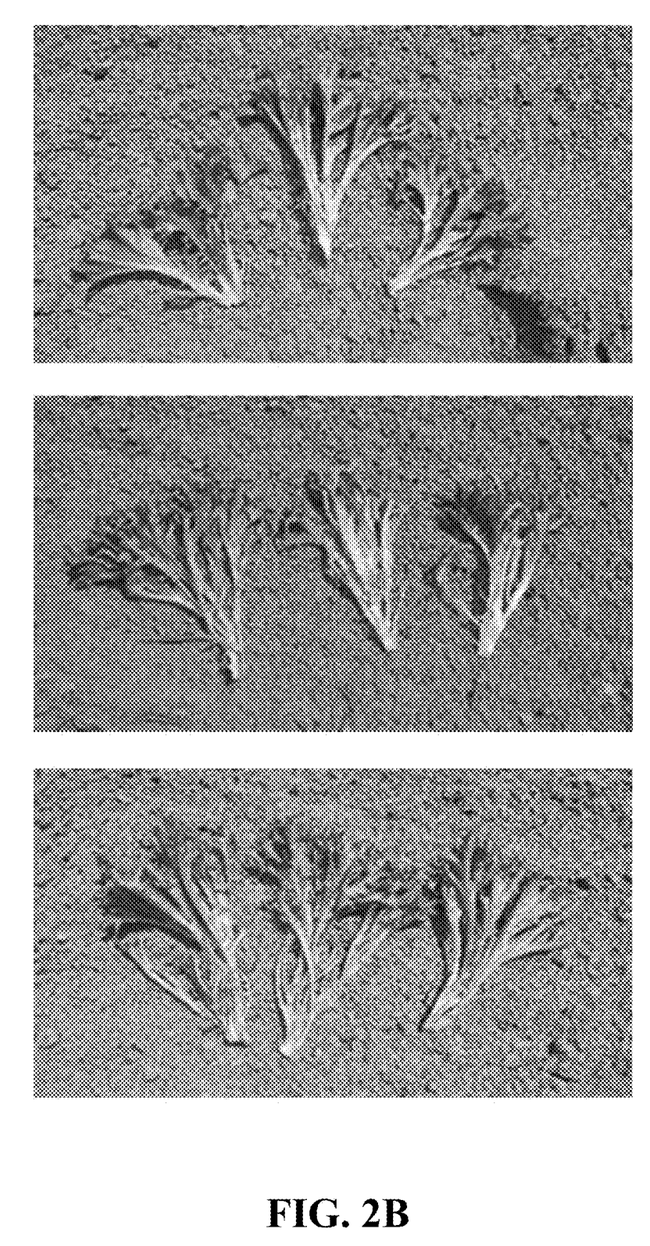
FIG. 2B shows a side-by-side comparison of harvest-mature outer leaves from lettuce varieties 'Ezpark' (top), 'Eztron (middle), and 'Ezrilla' (bottom).
Figure 2C:
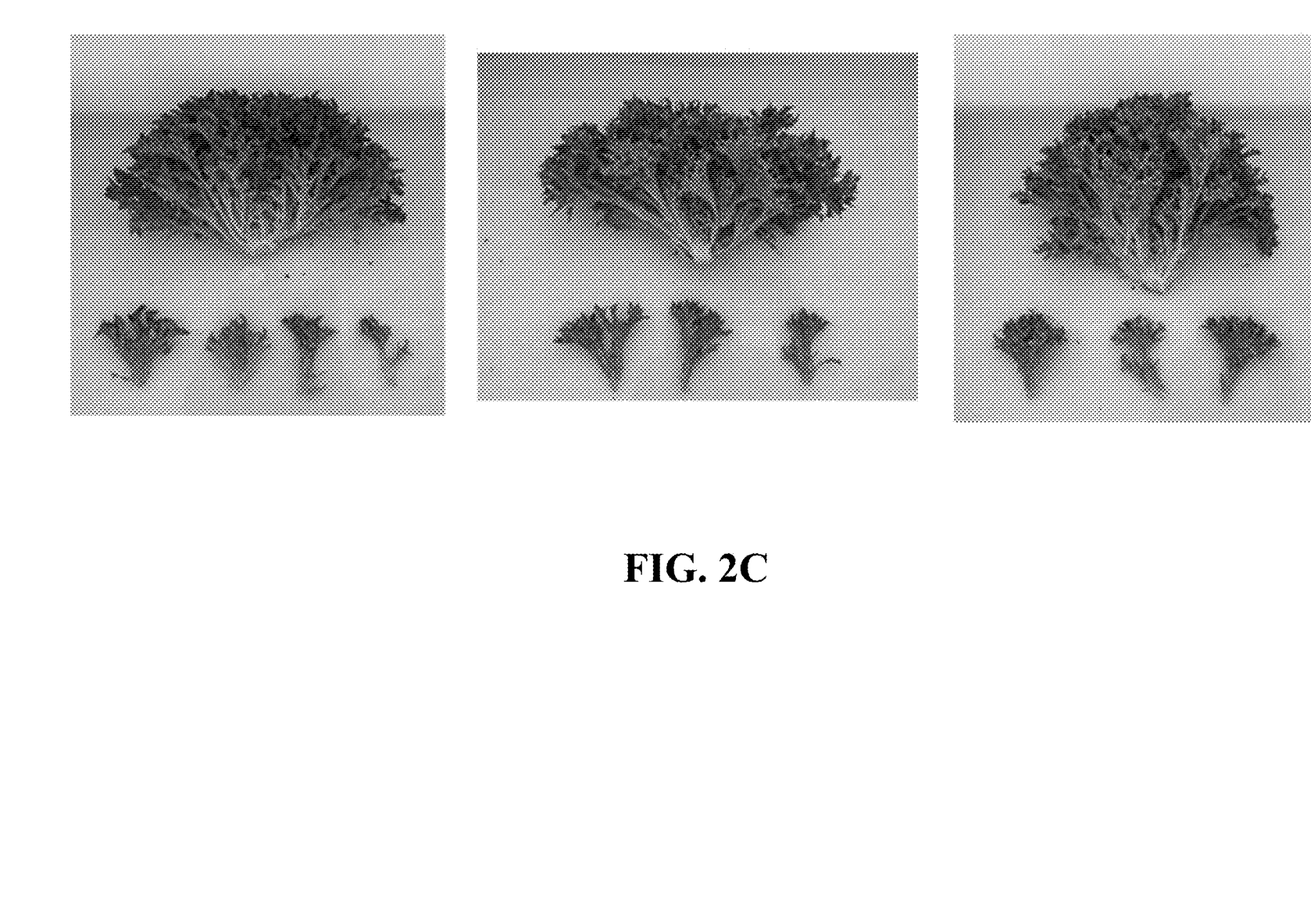
FIG. 2C shows a side-by-side comparison of longitudinal cross-sections and outer leaves of harvest mature plants of lettuce varieties 'Ezpark' (left), 'Eztron (middle), and 'Ezrilla' (right).
Figure 2D:
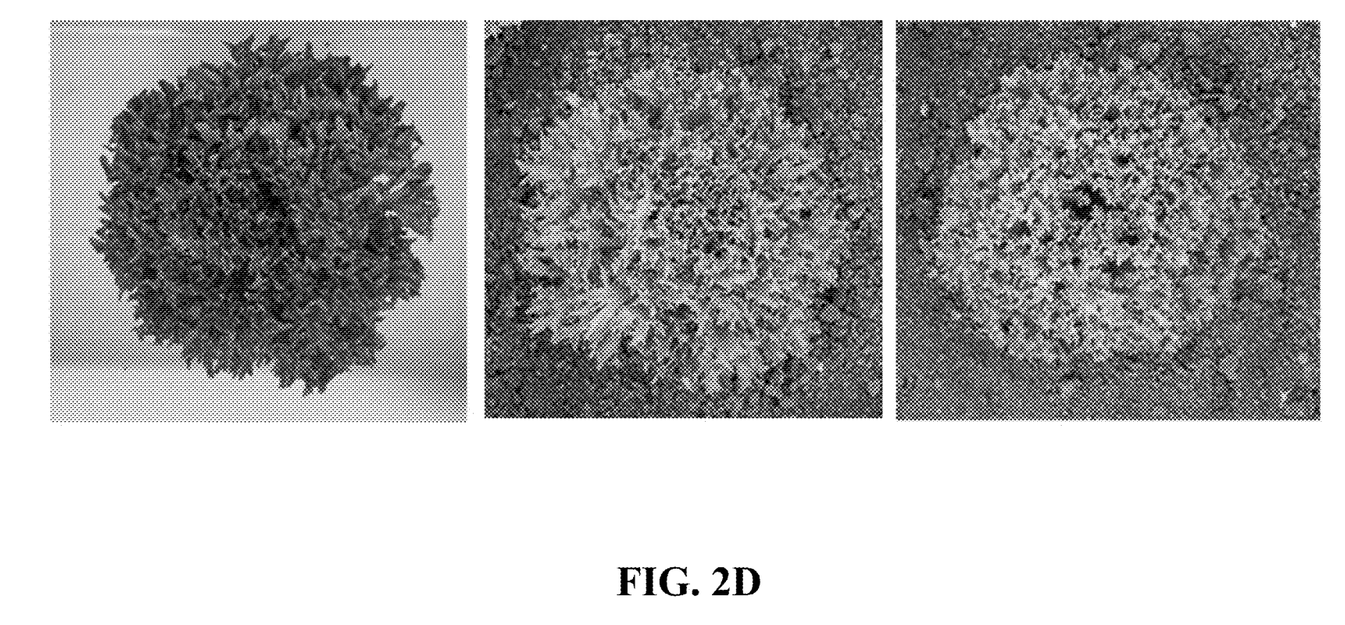
FIG. 2D shows a side-by-side comparison of top views of whole plants of lettuce varieties 'Ezpark' (left), 'Eztron' (middle), and 'Ezrilla' (right).

Lettuce variety 'Ezpark' is a cutting (i.e., leaf) lettuce variety with medium green colored leaves of moderate glossiness. 'Ezpark' is suitable for greenhouse and open field cultivation. Lettuce variety 'Ezpark' is resistant to lettuce leaf aphid (*Nasonovia ribisnigri*) biotype Nr:0, downy mildew (*Bremia lactucae*) strains Bl-EU:16-36; and susceptible to lettuce mosaic virus (LMV), lettuce die-back (TBSV), Lettuce root aphid (*Pemphigus bursarius*) (Pb) and *fusarium* wilt (*Fusarium oxysporum* f. sp. *lactucae*) (Fol) race 1 downy mildew (*Bremia lactucae*) strain B1-EU:17. In addition, lettuce variety 'Ezpark' is tolerant to side shoots; and moderately tolerant to tipburn and internal rib necrosis. FIG. 1A depicts whole plants and harvest-mature outer leaves of lettuce variety 'Ezpark', FIG. 1B depicts a top view of a whole plant of lettuce variety 'Ezpark', FIG. 1C depicts a longitudinal section of a harvest mature plant of lettuce variety 'Ezpark', and FIG. 1D depicts harvest-mature outer leaves of lettuce variety 'Ezpark'. Lettuce variety 'Ezpark' is the result of numerous generations of plant selections chosen for its incised leaves, tolerance to bolting during the summer season, yield, and good field holding, which make it suitable for year-round production.

The variety has shown uniformity and stability for the traits, within the limits of environmental influence for the traits. It has been self-pollinated a sufficient number of generations with careful attention to uniformity of plant type. The line has been increased with continued observation for uniformity.

Objective Description of the Variety 'Ezpark'

The data which define these characteristics is based on observations taken in Allonnes, France. The objective description of 'Ezpark' was taken from plants nine weeks after transplanting. Lettuce variety 'Ezpark' has the folloring morphologic and other characteristics:

Lettuce variety 'Ezpark' has the following morphologic and other characteristics:
  Plant type: Cutting (i.e., leaf)
  Seed:
    Color: Black (grey brown)
  Cotyledon to fourth leaf stage:
    Anthocyanin distribution: Absent
  Leaves at 10-12 leaf stage:
    Attitude: Erect
  Mature leaves:
    Incision depth (deepest penetration of the margin): Deep
    Indentation (finest divisions of the margin): Deeply
    Undulation of apical margin: Moderate
    Green color: Medium green
    Anthocyanin distribution: Absent
    Leaf glossiness: Moderate
    Leaf thickness: Intermediate
    Blistering: Absent or slight Plant:
    Plant shape: Non-heading
    Plant size class: Medium
    Plant firmness: Loose
  Butt:
    Butt shape: Rounded
    Midrib: Moderately raised
  Bolting:
    Class: Medium to late
  Growth condition:
    Type of culture: Both greenhouse and open field
  Disease/Pest Resistance:
    Lettuce mosaic virus (LMV) race 1: Susceptible
    Lettuce die-back (Tomato bushy stunt virus) (TBSV): Susceptible
    Downy mildew (*Bremia lactucae*) (Bl): Resistant to races B1-EU:16-36, and susceptible to race B1-US: 37
    *Fusarium* wilt (*Fusarium oxysporum* f. sp. *lactucae*) (Fol) race 1: Susceptible
    Lettuce leaf aphid (*Nasonovia ribisnigri*) biotype 0 (Nr: 0): Resistant
  Response to stresses:
    Tipburn: Moderately tolerant
    Side shoots: Tolerant
    Internal rib necrosis: Moderately tolerant Comparisons to Other Lettuce Varieties Table 1 below compares a characteristic of lettuce variety 'Ezpark' with the lettuce variety 'Eztron' (U.S. Pat. No. 11,089,751). Column 1 lists the characteristic, column 2 shows the characteristic for lettuce variety 'Ezpark', and column 3 shows the characteristic for lettuce variety 'Eztron'. FIGS. 2A-2D show side-by-side comparisons of whole plants (FIG. 2A), harvest-mature outer leaves (FIG. 2B), longitudinal cross-sections and outer leaves (FIG. 2C), and top views of whole plants (FIG. 2D) of lettuce varieties 'Ezpark' (left) and 'Eztron' (middle).

TABLE 1

| Characteristic | 'Ezpark' | 'Eztron' |
| --- | --- | --- |
| Time of bolting under long day conditions | Medium to late | Medium |
| Leaf attitude at 10-12 leaf stage | Erect | Semi-erect |
| Leaf blistering | Absent or slight | Slightly blistered |

Table 2 below compares a characteristic of lettuce variety 'Ezpark' with the lettuce variety 'Ezrilla' (U.S. Pat. No. 11,089,751). Column 1 lists the characteristic, column 2 shows the characteristic for lettuce variety 'Ezpark', and column 3 shows the characteristic for lettuce variety 'Ezrilla'. FIGS. 2A-2D show side-by-side comparisons of whole plants (FIG. 2A), harvest-mature outer leaves (FIG. 2B), longitudinal cross-sections and outer leaves (FIG. 2C), and top views of whole plants (FIG. 2D) of lettuce varieties 'Ezpark' (left) and 'Ezrilla' (right).

TABLE 2

| Characteristic | 'Ezpark' | 'Ezrilla' |
| --- | --- | --- |
| Leaf thickness | Intermediate | Thin |
| Leaf attitude at | Erect | Prostrate |

TABLE 2-continued

| Characteristic | 'Ezpark' | 'Ezrilla' |
|---|---|---|
| 10-12 leaf stage | | |
| Leaf glossiness | Moderate | Glossy |
| Leaf blistering | Absent or slight | Slightly blistered |
| Leaf indentation (finest divisions of the margin) | Smooth | Deeply dentate |
| Bolting class | Medium to late | Very late |

FURTHER EMBODIMENTS

Gene Conversions

When the term "lettuce plant" is used in the context of the present disclosure, this also includes any gene conversions of that variety. The term "gene converted plant" as used herein refers to those lettuce plants which are developed by backcrossing, genetic engineering, or mutation, where essentially all of the desired morphological and physiological characteristics of a variety are recovered in addition to the one or more genes transferred into the variety via the backcrossing technique, genetic engineering, or mutation. Backcrossing methods can be used with the present disclosure to improve or introduce a characteristic into the variety. The term "backcrossing" as used herein refers to the repeated crossing of a hybrid progeny back to the recurrent parent, i.e., backcrossing 1, 2, 3, 4, 5, 6, 7, 8, 9, or more times to the recurrent parent. The parental lettuce plant which contributes the gene for the desired characteristic is termed the "nonrecurrent" or "donor parent." This terminology refers to the fact that the nonrecurrent parent is used one time in the backcross protocol and therefore does not recur. The parental lettuce plant to which the gene or genes from the nonrecurrent parent are transferred is known as the recurrent parent, as it is used for several rounds in the backcrossing protocol (Poehlman & Sleper (1994) and Fehr (1993)). In a typical backcross protocol, the original variety of interest (recurrent parent) is crossed to a second variety (nonrecurrent parent) that carries the gene of interest to be transferred. The resulting progeny from this cross are then crossed again to the recurrent parent and the process is repeated until a lettuce plant is obtained where essentially all of the desired morphological and physiological characteristics of the recurrent parent are recovered in the converted plant, in addition to the transferred gene from the nonrecurrent parent.

The selection of a suitable recurrent parent is an important step for a successful backcrossing procedure. The goal of a backcross protocol is to alter or substitute a trait or characteristic in the original line. To accomplish this, a gene of the recurrent variety is modified or substituted with the desired gene from the nonrecurrent parent, while retaining essentially all of the rest of the desired genetic, and therefore the desired physiological and morphological, constitution of the original line. The choice of the particular nonrecurrent parent will depend on the purpose of the backcross. One of the major purposes is to add some commercially desirable, agronomically important trait to the plant. The exact backcrossing protocol will depend on the characteristic or trait being altered, which will determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many gene traits have been identified that are not regularly selected in the development of a new line but that can be improved by backcrossing techniques. Examples of these traits include, but are not limited to, male sterility, modified fatty acid metabolism, modified carbohydrate metabolism, herbicide resistance, resistance for bacterial, fungal, or viral disease, insect resistance, enhanced nutritional quality, industrial usage, yield stability, and yield enhancement. These genes are generally inherited through the nucleus. Several of these gene traits are described in U.S. Pat. Nos. 5,777,196, 5,948,957, and 5,969,212, the disclosures of which are specifically hereby incorporated by reference.

Tissue Culture

Further reproduction of the variety can occur by tissue culture and regeneration. Tissue culture of various tissues of lettuce and regeneration of plants therefrom is well known and widely published. For example, reference may be had to Teng, et al., HortScience, 27:9, 1030-1032 (1992); Teng, et al., HortScience, 28:6, 669-1671 (1993); Zhang, et al., Journal of Genetics and Breeding, 46:3, 287-290 (1992); Webb, et al., Plant Cell Tissue and Organ Culture, 38:1, 77-79 (1994); Curtis, et al., Journal of Experimental Botany, 45:279, 1441-1449 (1994); Nagata, et al., Journal for the American Society for Horticultural Science, 125:6, 669-672 (2000); and Ibrahim, et al., Plant Cell Tissue and Organ Culture, 28(2), 139-145 (1992). It is clear from the literature that the state of the art is such that these methods of obtaining plants are routinely used and have a very high rate of success. Thus, another aspect of this disclosure is to provide cells which upon growth and differentiation produce lettuce plants having the physiological and morphological characteristics of variety 'Ezpark'.

As used herein, the term "tissue culture" indicates a composition containing isolated cells of the same or a different type or a collection of such cells organized into parts of a plant. Exemplary types of tissue cultures are protoplasts, calli, meristematic cells, and plant cells that can generate tissue culture that are intact in plants or parts of plants, such as leaves, pollen, embryos, roots, root tips, anthers, pistils, flowers, seeds, petioles, suckers, and the like. Means for preparing and maintaining plant tissue culture are well known in the art. By way of example, a tissue culture containing organs has been used to produce regenerated plants. U.S. Pat. Nos. 5,959,185, 5,973,234, and 5,977,445 describe certain techniques, the disclosures of which are incorporated herein by reference.

Additional Breeding Methods

The disclosure is also directed to methods for producing a lettuce plant by crossing a first parent lettuce plant with a second parent lettuce plant where the first or second parent lettuce plant is a lettuce plant of variety 'Ezpark'. Further, both first and second parent lettuce plants can come from lettuce variety 'Ezpark'. Thus, any such methods using lettuce variety 'Ezpark' are part of the disclosure: selfing, backcrosses, hybrid production, crosses to populations, and the like. All plants produced using lettuce variety 'Ezpark' as at least one parent are within the scope of this disclosure, including those developed from varieties derived from lettuce variety 'Ezpark'. Advantageously, this lettuce variety could be used in crosses with other, different, lettuce plants to produce the first generation ($F_1$) lettuce hybrid seeds and plants with superior characteristics.

The variety of the disclosure can also be used for transformation where exogenous genes are introduced and expressed by the variety of the disclosure. Genetic variants created either through traditional breeding methods using lettuce variety 'Ezpark', or through transformation of variety 'Ezpark' by any of a number of protocols known to those of skill in the art are intended to be within the scope of this disclosure. For instance, transformation of variety 'Ezpark' may be achieved by transformation of plotoplasts using methods based on calcium phosphate precipitation, polyethylene glycol treatment, electroporation, and combinations of these treatments (see, e.g., Potrykus et al., 1985; Omirulleh et al., 1993; Fromm et al., 1986; Uchimiya et al., 1986; Marcotte et al., 1988). Transformation of plants and expression of foreign genetic elements is exemplified in Choi et al. (1994) and Ellul et al. (2003). Direct uptake of DNA into protoplasts using CaCl2 precipitation, polyvinyl alcohol, or poly-L-ornithine has also been reported (see, e.g., Hain et al., 1985 and Draper et al., 1982). Electroporation of protoplasts and whole cells and tissues have also been described (see, e.g., Saker et al., 1998; Donn et al., 1990; D'Halluin et al., 1992; and Laursen et al., 1994; Chupean et al., 1989).

The following describes breeding methods that may be used with lettuce variety 'Ezpark' in the development of further lettuce plants. One such embodiment is a method for developing variety 'Ezpark' progeny lettuce plants in a lettuce plant breeding program, by: obtaining the lettuce plant, or a part thereof, of variety 'Ezpark' utilizing said plant or plant part as a source of breeding material, and selecting a lettuce variety 'Ezpark' progeny plant with molecular markers in common with variety 'Ezpark' and/or with morphological and/or physiological characteristics selected from the characteristics listed in the section entitled "Objective description of the variety 'Ezpark'." Breeding steps that may be used in the lettuce plant breeding program include pedigree breeding, backcrossing, mutation breeding, and recurrent selection. In conjunction with these steps, techniques such as RFLP-enhanced selection, genetic marker enhanced selection (for example, SSR markers), and the making of double haploids may be utilized.

Another method involves producing a population of lettuce variety 'Ezpark' progeny lettuce plants, by crossing variety 'Ezpark' with another lettuce plant, thereby producing a population of lettuce plants, which, on average, derive 50% of their alleles from lettuce variety 'Ezpark'. A plant of this population may be selected and repeatedly selfed or sibbed with a lettuce variety resulting from these successive filial generations. One embodiment of this disclosure is the lettuce variety produced by this method and that has obtained at least 50% of its alleles from lettuce variety 'Ezpark'. One of ordinary skill in the art of plant breeding would know how to evaluate the traits of two plant varieties to determine if there is no significant difference between the two traits expressed by those varieties. For example, see Fehr and Walt, *Principles of Variety Development*, pp. 261-286 (1987). Thus, the disclosure includes lettuce variety 'Ezpark' progeny lettuce plants containing a combination of at least two variety 'Ezpark' traits selected from those listed in the section entitled "Objective description of the variety 'Ezpark'," or listed in the Summary, so that said progeny lettuce plant is not significantly different for said traits than lettuce variety 'Ezpark' as determined at the 5% significance level when grown in the same environmental conditions. Using techniques described herein, molecular markers may be used to identify said progeny plant as a lettuce variety 'Ezpark' progeny plant. Mean trait values may be used to determine whether trait differences are significant, and preferably the traits are measured on plants grown under the same environmental conditions. Once such a variety is developed, its value is substantial since it is important to advance the germplasm base as a whole in order to maintain or improve traits such as yield, disease resistance, pest resistance, and plant performance in extreme environmental conditions.

Progeny of lettuce variety 'Ezpark' may also be characterized through their filial relationship with lettuce variety 'Ezpark' as, for example, being within a certain number of breeding crosses of lettuce variety 'Ezpark'. A breeding cross is a cross made to introduce new genetics into the progeny, and is distinguished from a cross, such as a self or a sib cross, made to select among existing genetic alleles. The lower the number of breeding crosses in the pedigree, the closer the relationship between lettuce variety 'Ezpark' and its progeny. For example, progeny produced by the methods described herein may be within 1, 2, 3, 4, or 5 breeding crosses of lettuce variety 'Ezpark'.

As used herein, the term "plant" includes plant cells, plant protoplasts, plant cell tissue cultures from which lettuce plants can be regenerated, plant calli, plant clumps, and plant cells that are intact in plants or parts of plants, such as leaves, pollen, embryos, cotyledons, hypocotyl, roots, root tips, anthers, pistils, flowers, ovules, seeds, stems, and the like.

The use of the terms "a," "an," and "the," and similar referents in the context of describing the disclosure (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

While a number of exemplary aspects and embodiments have been discussed above, those of skill in the art will recognize certain modifications, permutations, additions, and sub-combinations thereof. It is therefore intended that the following appended claims and claims hereafter introduced are interpreted to include all such modifications, permutations, additions, and sub-combinations as are within their true spirit and scope.

DEPOSIT INFORMATION

Lettuce Variety 'Ezpark'

A deposit of at least 625 seeds of the lettuce variety 'Ezpark' was made with the National Collection of Industrial, Food and Marine Bacteria Ltd. (NCIMB Ltd), Wellheads Place, Dyce, Aberdeen AB21 7 GB, United Kingdom, and assigned NCIMB Number 44138. The seeds deposited with the NCIMB on Apr. 20, 2023 were obtained from the seed of the variety maintained by Enza Zaden USA, Inc., 7 Harris Place, Salinas, California 93901, United States since prior to the filing date of the application. Access to this deposit will be available during the pendency of this application to persons determined by the Commissioner of Patents and Trademarks to be entitled thereto under 37 C.F.R. § 1.14 and 35 U.S.C. § 122. Upon issuance, the Applicant will make the deposit available to the public consistent with all of the requirements of 37 C.F.R. § 1.801-1.809. This deposit of the lettuce variety 'Ezpark' will be maintained in the NCIMB, which is a public depository, for a period of 30 years, or at least 5 years after the most recent request for a sample of the deposit, or for the effective life of the patent, whichever is longer, and will be replaced if it becomes nonviable during that period. Applicant has no authority to waive any restrictions imposed by law on the transfer of biological material or its transportation in commerce. Applicant does not waive any infringement of rights granted under this patent or under the Plant Variety Protection Act (7 USC 2321 et seq.).

The invention claimed is:

1. A lettuce seed designated as 'Ezpark', representative sample of seed having been deposited under NCIMB Accession Number 44138.

2. A lettuce plant produced by growing the seed of claim 1.

3. A plant part from the plant of claim 2.

4. The plant part of claim 3, wherein said part is a leaf, an ovule, a pollen grain, or a cell.

5. The plant part of claim 4, wherein said part is a leaf.

6. A lettuce plant having all or essentially all the physiological and morphological characteristics of the lettuce plant of claim 2.

7. A plant part from the plant of claim 6.

8. The plant part of claim 7, wherein said part is a leaf, an ovule, a pollen grain, or a cell.

9. The plant part of claim 8, wherein said part is a leaf.

10. An $F_1$ hybrid lettuce plant having the lettuce plant of claim 2 as a parent.

11. A pollen grain or an ovule of the plant of claim 2.

12. A protoplast produced from the plant of claim 2.

13. A tissue or cell culture produced from protoplasts or cells from the plant of claim 2, wherein said cells or protoplasts are produced from a plant part selected from the group consisting of root, root tip, meristematic cell, stem, hypocotyl, petiole, cotyledon, leaf, flower, anther, pollen, pistil, and fruit.

14. A lettuce plant regenerated from the tissue culture of claim 13, wherein:
the plant has all or essentially all of the morphological and physiological characteristics of a lettuce plant produced by growing seed designated as 'Ezpark', representative sample of seed having been deposited under NCIMB Accession Number 44138.

15. A method of making lettuce seeds, said method comprising crossing the plant of claim 2 with another lettuce plant and harvesting seed therefrom.

16. A method of producing a lettuce leaf, said method comprising growing the plant of claim 2 until it produces at least one leaf, and harvesting the leaf.

17. A method of producing 'Ezpark'-derived lettuce seeds, comprising the steps:
(a) crossing a lettuce designated as 'Ezpark' with itself or a second lettuce plant,
representative sample of seed of 'Ezpark' having been deposited under NCIMB Accession Number 44138; and
(b) whereby seed of an 'Ezpark'-derived lettuce plant forms.

18. The method of claim 17 further comprising:
(c) crossing a plant grown from 'Ezpark'-derived lettuce seed with itself or a second lettuce plant to yield additional 'Ezpark'-derived lettuce seed;
(d) growing the additional 'Ezpark'-derived lettuce seed of step (c) to yield additional 'Ezpark'-derived lettuce plants; and
(e) repeating the crossing and growing of steps (c) and (d) for an additional 3-10 generations to generate further 'Ezpark'-derived lettuce plants.

* * * * *